US006445946B1

United States Patent
Hutten

(10) Patent No.: US 6,445,946 B1
(45) Date of Patent: Sep. 3, 2002

(54) APPARATUS FOR DETECTING FUSION EVENTS UPON ELECTROSTIMULATION OF THE HEART

(75) Inventor: Helmut Hutten, Graz (AT)

(73) Assignees: Biotronik Mess-und Therapiegerate GmbH & Co. Ingenieurburo Berlin, Berlin (DE); Cortronik Mess-und Therapiegerate GmbH, Graz (AT)

( * ) Notice: Subject to any disclaimer, the term of this patent is extended or adjusted under 35 U.S.C. 154(b) by 10 days.

(21) Appl. No.: 09/632,896

(22) Filed: Aug. 7, 2000

(30) Foreign Application Priority Data

Aug. 6, 1999 (DE) .......................................... 199 38 376

(51) Int. Cl.[7] .......................................... A61B 5/0468
(52) U.S. Cl. .......................................... 600/510; 607/27
(58) Field of Search ................. 128/923; 600/508–510; 607/9, 11, 25, 27

(56) References Cited

U.S. PATENT DOCUMENTS

| 5,749,906 A | 5/1998 | Kieval et al. ................... 607/9 |
| 5,836,889 A | 11/1998 | Wyborny et al. ........... 600/509 |

FOREIGN PATENT DOCUMENTS

| DE | 44 16 779 | 11/1995 |
| DE | 196 09 411 | 9/1997 |
| EP | 0 398 488 | 11/1990 |
| EP | 0 570 895 | 11/1993 |
| EP | 0 842 675 | 5/1998 |
| WO | WO 92/05836 | 4/1992 |
| WO | WO 99/65569 | 12/1999 |

*Primary Examiner*—Kennedy Schaetzle
*Assistant Examiner*—Kristen Droesch
(74) *Attorney, Agent, or Firm*—Christie, Parker & Hale, LLP

(57) ABSTRACT

A cardiological apparatus is provided having a sensor (1) for picking up electrical signals from a heart and a signal processor connected to the sensor (1) and which is adapted to process signals received from the sensor (1) and includes a pre-processor, wherein the processor includes a reference time generator (8) which is adapted to output a time signal upon the occurrence of a periodically recurring signal feature, averaging features (11, 12, 22, 6) which are adapted to form a signal portion which is averaged over a plurality of signal portions between each two time signals, an average store (7) which is adapted to store the average values, a parameter determining feature (9), and scatter value determining features (31) which are adapted to output a scatter value for time-successive signals.

9 Claims, 1 Drawing Sheet

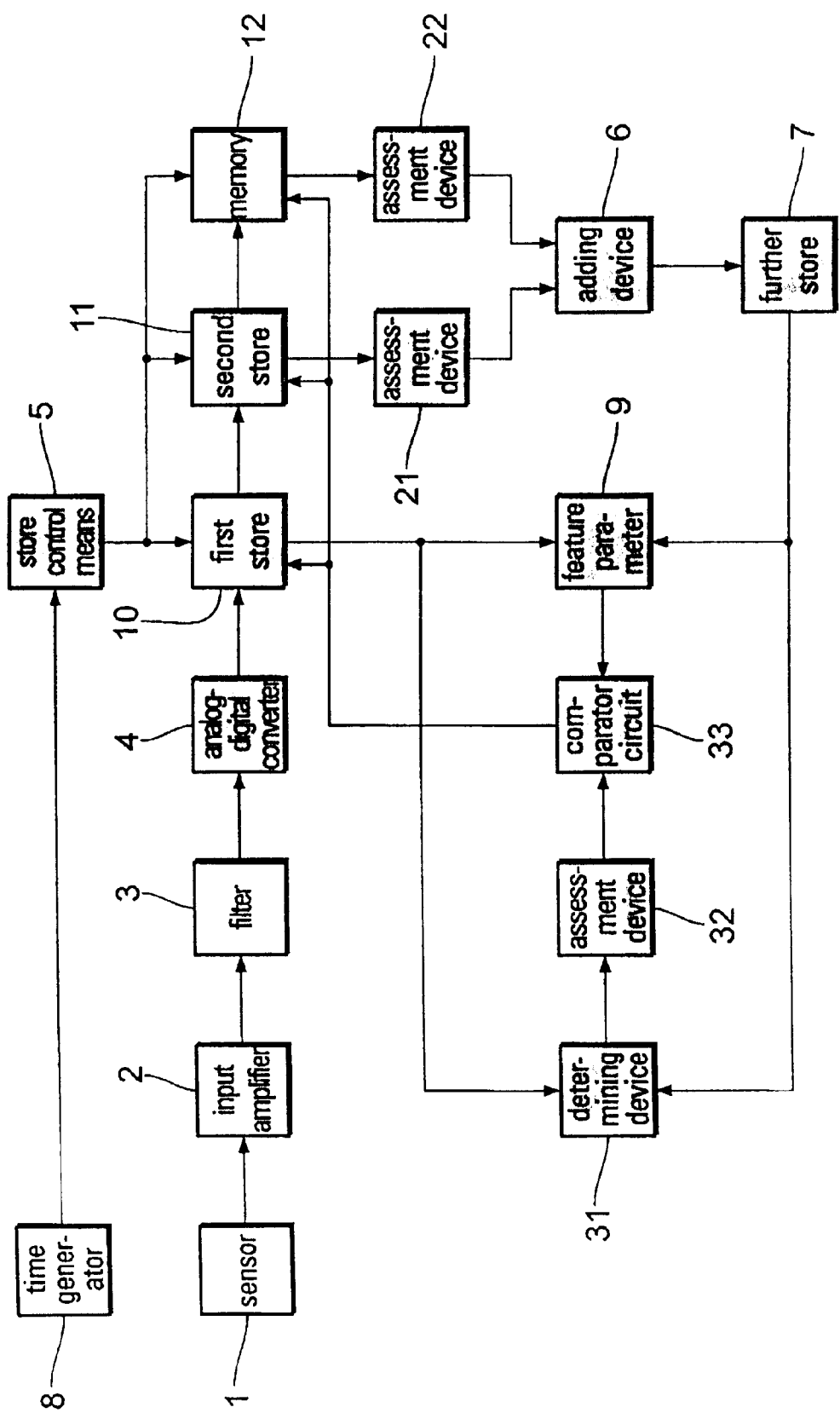

APPARATUS FOR DETECTING FUSION EVENTS UPON ELECTROSTIMULATION OF THE HEART

CROSS-REFERENCE TO RELATED APPLICATION

This application claims priority of German patent application number 199 38 376.6, filed Aug. 6, 1999.

BACKGROUND OF THE INVENTION

The invention concerns a cardiological apparatus having a sensor for picking up electrical signals from the heart and signal processing means which are connected to the sensor and which are adapted to process signals received from the sensor and include pre-processing means.

The state of the art discloses apparatuses which are used either for detecting spontaneous excitations of the heart or for detecting stimulated excitations of the heart, which are triggered by an electrical stimulus.

Those known apparatuses are based on the aspect that the variation in respect of time of that electrical signal of the heart, which accompanies the progress of the excitation, contains typical features which make it possible to arrive at a distinction between spontaneous excitations and stimulated excitations.

Electrical cardiac pacemakers of different embodiments serve for stimulation of the heart in situations in which either there is a disturbance to the physiological occurrence and/or propagation of the excitation or therapeutic considerations indicate the stimulation of excitations. The operational control for providing for control in respect of time of the electrical cardiac pacemaker must be capable of recognizing whether and when a spontaneous excitation occurs. In particular the situation is not to entail any adverse effect on the pump action of the heart, which is produced by the excitation, due to a stimulation which occurs at the wrong time.

In the heart the location of spontaneous excitation formation and the location where spontaneous excitation formation is detected by measurement procedures are separated in respect of space. Usually ventricular pacemaker electrodes are implanted in the tip of the ventricle. Ventricular contractions which are triggered by a pacemaker due to electrical stimulation in the tip of the ventricle are propagated in an excitation front which moves from the tip of the ventricle over the entire periphery of the ventricle in the direction of the AV-node of a heart. Ventricular contractions of the ventricle, which are triggered by the heart itself, in contrast originate from the sinus node in the atrium of the heart and are transmitted into the ventricle by way of the AV-node. That means that, in the event of a contraction caused by the heart itself, the ventricular excitation front is triggered by the AV-node and moves in the direction of the tip of the ventricle. Accordingly, at the pacemaker electrode which is placed there, it can also be detected only relatively late after the commencement of its occurrence, namely after the expiry of the so-called latency time. As an excitation is propagated in the heart at relatively low speed, it can happen that electrical stimulation occurs although spontaneous excitation has already taken place, as the spontaneous excitation had not yet occurred at that time at which electrical stimulation was triggered. In that case, two excitation fronts move towards each other, one starting from the location of spontaneous excitation and the other from the location of electrical stimulation. Excitation of a part of the cardiac tissue is effected by spontaneous excitation, while excitation of the other part of the cardiac tissue is effected by electrical stimulation. Such events are referred to as fusion events. Fusion events can influence the electrophysiological co-ordination which forms the basis for the pump action of the heart, and therewith the mechanical processes involved and therewith the pump output and efficiency.

SUMMARY OF THE INVENTION

The object of the present invention is to detect fusion events of that kind.

In accordance with the invention that object is attained by an apparatus of the kind set forth in the opening part of this specification, the signal processing means of which include:

- a reference time generator (8) which is adapted to output a time signal upon the occurrence of a periodically recurring signal feature,
- averaging means (11, 12, 21, 22, 6) which are adapted to form a signal portion which is averaged over a plurality of signal portions between each two time signals, and are connected to the pre-processing means (2, 3, 4) and the reference time generator (8),
- an average store (7) which is adapted to store the average values and which is connected to the averaging means, and
- parameter determining means (9) which are connected to the pre-processing means (2, 3, 4) and the average store and which are adapted to ascertain a parameter characterizing a signal portion.

Advantageous alternative configurations are optionally distinguished by the following features:

- the parameter determining means are adapted to derive the parameter from the respective signal portion last detected by the sensor;
- the parameter determining means are adapted to derive the parameter from the averaged signal portion;
- the signal processing means include comparison means which are connected to the parameter determining means and a limit value store for comparing the derived parameter and a limit value stored in the limit value store and are adapted to output a fusion signal;
- the signal processing means include scatter value determining means which are adapted to output a scatter value for time-successive signals and which are connected to the pre-processing means;
- the scatter value determining means are connected to the average value store;
- the signal processing means additionally include limit value determining means which are adapted to determine the limit value from the scatter values and are connected to the scatter value determining means and to a limit value store. In that respect the limit value store can be an integral component of the limit value determining means;
- the pre-processing means include an instantaneous signal store for the respective signal portion last detected by the sensor. In that case the units connected downstream of the signal pre-processing operation access the instantaneous signal store of the pre-processing means for the parameter-determining operation and for the averaging operation and also for the scatter value-determining operation;
- the signal processing means include inhibitor means which are adapted to suppress such signal portions for further signal processing, for which comparison means output a fusion signal. Signals as a result of fusion events are therefore not taken into consideration for the averaging operation and for the scatter value-determining operation; and the inhibitor means are such that they erase the instantaneous signal store when a fusion signal occurs.

The invention embraces the technical teaching that, upon the detection of a fusion event, such relationships must also be taken into account, which go beyond direct association with the mechanical efficiency and output of the heart. In particular the invention takes into consideration the secure knowledge that individual particularities such as the shape and size of the heart, the measurement location for any spontaneous depolarization which may possibly occur and pathophysiological disturbances can have an effect on loss of the measurements signal.

The invention is also based on the realization that signals which occur in succession in a biological system never have precisely the same fine signal structure but may involve certain deviations, the cause of which does not exclusively have to be the occurrence of a fusion event.

The signals which are used to detect fusion events are electrical signals which are obtained in known manner with a sensor which is conductively connected to an apparatus suitable for pre-processing and further processing of those signals. The pre-processing operation, for example amplification and frequency-determining filtering to remove signal components which are not information-relevant in the sense of detecting a fusion event can be effected in a manner in accordance with the state of the art. Some of the implantable cardiac pacemakers corresponding to the state of the art, with a sensing channel, are enabled for that pre-processing. Pre-processing of the signal can be implemented in analog or digital form.

The basis for the invention is an apparatus which makes it possible to extract those feature parameters which are characteristic of the occurrence of a fusion event, from an electrical signal which is caused by a heart excitation and which subjected to suitable further processing. The feature extraction procedure is advantageously implemented by digital processing, but in principle it can also be effected by an analog processing procedure or a hybrid analog-digital processing procedure.

The invention is implemented by an apparatus which is provided with the capability of averaging from the individual signals which occur in succession in respect of time. The averaging operation can be implemented for the entire configuration of the individual signals, insofar as it is relevant for detecting fusion events, or for given features which were obtained from the individual signals and which are relevant in terms of the detection of fusion events. The features obtained from the individual signals can be one or more features.

The operation of ascertaining the average value can be based on a time-related assessment function. The apparatus also has the capability of forming a scatter value from the deviation of the individual signals or the features obtained therefrom from the average value. That scatter value is a measurement in respect of the deviation of the individual signals and the features obtained therefrom, from the average value. The claim of the invention to affording adequate consideration being given to individual particularities is carried into effect by virtue of that averaging procedure.

Individual signals which are classified as fusion events are not taken into consideration either in the formation of the average value or in calculation of the scatter value. As the procedure for ascertaining the average value and the scatter value is implemented continuously, that satisfies the requirement, which is essential in the sense of the claim of the invention, for adaptation in respect of time to changing conditions which have effects on the fine signal structure.

Each freshly occurring individual signal is compared to the stored average value in regard to those features which are characteristic in respect of a fusion event. If the deviation exceeds a value which is established based on the scatter value as a limit value, the event is classified as a fusion event.

The subject-matter of the invention is therefore an apparatus for detecting fusion events which are caused by stimulation of the heart with an electrical cardiac pacemaker, wherein the apparatus ascertains feature parameters which are characteristic in respect of fusion events on the basis of continuous formation of average values with a time-related assessment function which can be adjusted as desired, compares them to the corresponding feature parameters derived from the individual signal which occurred last, and uses the deviation from a limit value on the basis of a scatter value which is also continuously ascertained by the apparatus according to the invention, as a decision criterion in respect of a fusion event.

This apparatus is optionally distinguished by the following features:

the time of the first zero-passage of the electrophysiological signal of heart excitation, which is detected by the sensor (1), is used as the feature parameter for detection of a fusion event;

the steepness of the electrophysiological signal of heart excitation, which is detected by the sensor (1), at the time of the first zero-passage, is used as a feature parameter for detection of a fusion event;

the time of each kink in the configuration of the electrophysiological signal of heart excitation, which is detected with the sensor (1), at which the initially rapid course of depolarization markedly changes to a slower course is used as a feature parameter for detection of a fusion event;

that time at which the electrophysiological signal of heart excitation, which is detected with the sensor, is at a maximum is used as a feature parameter for detection of a fusion event;

that time at which the electrophysiological signal of heart excitation, which is detected with the sensor, becomes zero again after excitation has expired, is used as a feature parameter for detection of a fusion event;

the maximum steepness in the configuration of the electrophysiological signal of heart excitation, which is detected with the sensor, at the return to the initial signal after heart excitation has expired or an auxiliary parameter derived from the maximum steepness is used as a feature parameter for detection of a fusion event;

a plurality of feature parameters are ascertained and used in joint assessment as a criterion for the occurrence of a fusion event;

the sensor for detecting the electrophysiological signal of heart excitation is used at the same time as an electrode for stimulation of the heart;

the detector for detecting the electrophysiological signal of heart excitation comprises a plurality of components;

the apparatus is completely implanted, in a housing suitable for that purpose, in the body of a human; and the apparatus is disposed jointly with an electrical cardiac pacemaker in a housing and completely implanted in a body of a human.

The FIGURE is a schematic of the essential functional units and their functional arrangement with which the classifying portion of the claim can be carried into effect.

DETAILED DESCRIPTION OF AN EXEMPLARY EMBODIMENT

The signal which is picked up by the sensor 1 as an expression of heart excitation, after suitable pre-processing which in the present example is effected in analog form by an input amplifier 2 and a filter 3, is passed to an analog-digital converter 4. Analog-digital conversion has to be effected at a sufficiently high sampling rate and with a sufficiently high level of amplitude discretisation so that this does not entail any falsification or elimination of the signal components which are essential for fusion detection.

The digitized signal obtained in that way is fed to a first memory or store 10 which must comprise a sufficient number of memory or storage cells so that it can receive all signal values which are required for further processing. Storage of the signal values which occur in succession in respect of time is effected in ordered form. Arranged downstream of the first store 10 is a second store 11 of a design configuration which substantially corresponds to the first store 10. The content of the first store 10 can be transferred in ordered form into the second store 11 by a control pulse which is generated in the store control means 5. A third store or memory 12 which is of a design configuration corresponding to the store 11 can be arranged downstream of the store 11. The store 12, with the occurrence of the control pulse at the output of the store control means 5, takes over the content of the second store 11 in ordered form.

The number N of the memories or stores which are arranged in succession in that way can be of any desired magnitude but must be at least equal to 2. With the occurrence of the control pulse at the output of the store control means 5, each store takes over in an ordered manner the content of the store which is disposed upstream thereof, but only the content of the store at the last location is lost with the occurrence of the control pulse.

The signal components contained in the successively arranged stores 11, 12 . . . 1N with the exception of the first store 10 are fed by way of assessment devices 21, 22 . . . 2N to an adding device 6. In that respect, each of the assessment devices is connected in the same manner to one of the stores, for example the second store 11 to the assessment device 21, the third store 12 to the assessment device 22 and so forth. Overall therefore there are as many assessment devices as there are stores, with the exception of the first store 10. It will be appreciated however that each assessment device can be provided with its own assessment factor of between 1 and 0 with suitable subdivision. In that way the content of each store 11, 12 . . . 1N can be multiplicatively weighted with an adjustable assessment factor before it is passed to the adding device 6. Connected on the downstream side of the adding device is a further store 7 which is of a design configuration like the stores 11, 12 . . . 1N. Therefore, after the addition operation has been carried out, the content of that store 7 contains a signal which represents the average value of the signals contained in the stores 11, 12 . . . 1N, which average was freshly formed with the occurrence of each individual signal and was ascertained on the basis of a weighting function which can be adjusted as desired. The time-related reference value which is required for time association of the various signal values of the successively occurring individual signals and thus for a correct averaging operation is derived from the leading edge of that stimulus which is outputted by the output amplifier 8 of the electrical cardiac pacemaker.

The comparison between the average value signal in the store 7 and the freshly occurred signal in the store 10 can relate to any feature which is characteristic in respect of a fusion event. That may equally well involve time features, for example the occurrence of characteristic points in the signal configuration as well as zero-passages, maxima, minima, instants of greatest positive or negative gradient in the signal configuration or differences in the signal morphology. The device for quantitatively ascertaining that feature parameter 9 uses circuits corresponding to the state of the art, for example for determining a zero-passage an amplitude discriminator or for determining the instant of maxima, minima or gradient parameters, the signal configuration which is differentiated in respect of time. Differences in signal morphology can be ascertained by correlation circuits. The device for quantitatively ascertaining that feature parameter 9 can advantageously be embodied by a microprocessor circuit.

As individual signals which successively occur in a biological system are never identical, a scatter value is additionally formed for that feature which is used for fusion detection, from the signals stored in the stores 11, 12 . . . 1N, in the scatter value determining device 31. That scatter value represents a measurement in respect of the scatter width of the individual signals without fusion events around that feature value which is formed adaptively and which is to be considered as a reference value for nonfusion events, by virtue of no consideration being given to fusion events. The scatter value determining device 31 can be embodied by circuits which correspond to the state of the art, advantageously by means of a microprocessor circuit.

The scatter value ascertained in the device 31 is converted in an assessment circuit 32 into that limit value, the exceeding of which is characteristic in respect of a fusion event. In the comparator circuit 33, the value ascertained in the device for quantitatively ascertaining the feature parameter 9 is compared with that which was ascertained as a limit value in the assessment circuit 32. A fusion event occurs when the output signal of the device 9 is greater than that of the device 32. When a fusion event has been detected, the content of the store 10 is set to zero and the stored content of the stores 11, 12 . . . 1N is prevented from being passed on. In that way the content of the average value store 7 and the scatter value determining device 31 are not changed by a fusion event.

What is claimed is:

1. A cardiological apparatus having a sensor (1) for detecting electrical signals from the heart and signal processing means which are connected to the sensor (1) and which are adapted to process signals received from the sensor (1) and include pre-processing means (2, 3, 4), characterized in that the signal processing means include:

a reference time generator (8) which is adapted to output a time signal upon the occurrence of a periodically recurring signal feature, averaging means (11, 12, 21, 22, 6) which are adapted to form an averaged signal portion which is averaged over a plurality of signal portions between each two time signals, and are connected to the pre-processing means (2, 3, 4) and the reference time generator (8), an average store (7) which is adapted to store average values and which is connected to the averaging means, parameter determining means (9) which are connected to the pre-processing means (2, 3, 4) and the average store and which are adapted to ascertain a parameter characterizing a signal portion, and scatter value determining means (31) which are adapted to output a scatter value for time-successive signals and which are connected to the pre-processing means (2, 3, 4).

2. Apparatus as set forth in claim 1 characterized in that the parameter determining means (9) are adapted to derive the parameter from the respective signal last detected by the sensor (1).

3. Apparatus as set forth in claim 1 or claim 2 characterized in that the parameter determining means (9) are adapted to derive the parameter from the averaged signal portion.

4. Apparatus as set forth in claim 1 characterized in that the signal processing means include comparison means (33) which are connected to the parameter determining means (9) and a limit value store for comparing the derived parameter and a limit value stored in the limit value store and are adapted to output a fusion signal.

5. Apparatus as set forth in claim 1 characterized in that the scatter value determining means (31) are connected to the average value store (7).

6. Apparatus as set forth in claim 1 characterized in that the signal processing means additionally include limit value determining means (32) which are adapted to determine the limit value from the scatter values and are connected to the scatter value determining means (31) and to a limit value store.

7. Apparatus as set forth in claim 1 characterized in that the pre-processing means (2, 3, 4) include an instantaneous signal store (10) for the respective signal last detected by the sensor (1).

8. Apparatus as set forth in claim 1 characterized in that the signal processing means include inhibitor means which are adapted to suppress such signal portions for further signal processing, for which comparison means (33) output a fusion signal.

9. Apparatus as set forth in claim 7 characterized in that the inhibitor means are such that they erase the instantaneous signal store (10) when a fusion signal occurs.

* * * * *